United States Patent
Kim et al.

(10) Patent No.: US 8,772,241 B2
(45) Date of Patent: Jul. 8, 2014

(54) PEPTIDE AND USE THEREOF

(75) Inventors: Hae Jin Kim, Daejeon (KR); Je Wook Lee, Daejeon (KR); Young Joon Kwon, Daejeon (KR); Eun Joung Moon, Daejeon (KR)

(73) Assignee: Ensoltek Co., Ltd., Daejeon (KR)

( * ) Notice: Subject to any disclaimer, the term of this patent is extended or adjusted under 35 U.S.C. 154(b) by 0 days.

(21) Appl. No.: 13/701,465

(22) PCT Filed: Jun. 22, 2011

(86) PCT No.: PCT/KR2011/004541
§ 371 (c)(1),
(2), (4) Date: Nov. 30, 2012

(87) PCT Pub. No.: WO2012/005668
PCT Pub. Date: Jan. 5, 2012

(65) Prior Publication Data
US 2013/0109626 A1    May 2, 2013

(30) Foreign Application Priority Data

Jun. 30, 2010 (KR) .................. 10-2010-0062467

(51) Int. Cl.
*A61K 38/08* (2006.01)
*A61K 38/18* (2006.01)
*C07K 7/06* (2006.01)
*C07K 14/495* (2006.01)

(52) U.S. Cl.
USPC .......................... 514/17.1; 514/8.9; 530/330

(58) Field of Classification Search
None
See application file for complete search history.

(56) References Cited

U.S. PATENT DOCUMENTS

| | | | |
|---|---|---|---|
| 5,955,343 | A | 9/1999 | Holmes et al. |
| 6,727,224 | B1 | 4/2004 | Zhang et al. |
| 2005/0037959 | A1* | 2/2005 | Cwirla et al. ............... 514/12 |
| 2009/0074876 | A1 | 3/2009 | Middleton-Hardie et al. |
| 2010/0136087 | A1 | 6/2010 | Ting et al. |

FOREIGN PATENT DOCUMENTS

| | | |
|---|---|---|
| CN | 101611051 A | 12/2009 |
| EP | 1400252 A1 | 3/2004 |
| WO | 00/02916 A2 | 1/2000 |
| WO | 02/062961 A2 | 8/2002 |
| WO | 2006/036826 A2 | 4/2006 |
| WO | WO 2009/097692 A1 * | 8/2009 |

OTHER PUBLICATIONS

Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*
Umlauf et al. Cartilage biology, pathology, and repair. Cell Mol Life Sci. Dec. 2010;67(24):4197-211.*
Clouet J et al., Drug Discovery Today (2009) 14:19/20, 913-925.
Gegout PP et al., Joint Bone Spine (2008) 669-671.
Derfoul A et al., Osteoarthritis Cartilage(2007) 15, 646-655.
Tiraloche G et al., Arthritis Rheum. (2005) 52, 1118-1128.
McAlindon TE et al., JAMA (2000) 283 (11): 1469-1475.
Zainal Z et al., Osteoarthritis Cartilage (2009) 17(7): 896-905.
Waddell DD et al., Arthroscopy (2010) 26(1):105-11.
Wang CT et al., J. Bone Joint Surg. Am. (2004) 86-A 538-545.
Glass GG Dis. Mon. (2006) 343-362.
Zhang W et al.,Ann. Rheum. Dis. (2004) 63, 901-907.
Frampton JE et al., Drugs (2007) 67(16):2433-72.
McDonough AL. PhysTher. (1982) 62(6): 835-9.
Shi S et al., J. Biol. Chem. (2009) 284 (1): 6697-6704.
Moore EE et al., Osteoarthritis Cartilage (2005) 13, 623-631.
Csaki Cet al., Ann Anat. (2008) 190(5): 395-412.
J. Kisiday, et al. "Self-assembling peptide hydrogel fosters chondrocyte extracellular matrix production and cell division: Implications for cartilage tissue repair." Proceedings of the National Academy of Sciences. vol. 99, No. 15, Jul. 23, 2002, pp. 9996-10001.
Shuguang Zhang, et al. "Peptide self-assembly in functional polymer science and engineering." Reactive & Functional Polymers. vol. 41, No. 1-3, 1999, pp. 91-102.
Paul W. Kopesky, et al. "Self-Assembling Peptide Hydrogels Modulate In Vitro Chondrogenesis of Bovine Bone Marrow Stromal Cells." Tissue Engineering Part A, vol. 16, No. 2, Feb. 1, 2010, pp. 465-477.

* cited by examiner

*Primary Examiner* — David Romeo
(74) *Attorney, Agent, or Firm* — Novick, Kim & Lee, PLLC; Jae Youn Kim

(57) ABSTRACT

The present invention provides a peptide represented by formula (I) of $X_1$-Leu-$X_2$-Leu-$X_3$ wherein $X_1$ represents Glu or Asp, $X_2$ represents His, Lys or Arg, $X_3$ represents Asp or Glu, with Glu, Asp, Leu, His, Lys and Arg being respectively glutamic acid, aspartic acid, leucine, histidine, lysine and arginine; or a pharmaceutically acceptable salt thereof; a composition for the treatment or prevention of at least one selected from cartilage damage and arthritis, containing the same peptide or a pharmaceutically acceptable salt thereof as an active ingredient; and a composition containing the same peptide or a pharmaceutically acceptable salt thereof and TGFβ1. The above-mentioned peptide or a pharmaceutically acceptable salt thereof is effective for the treatment and/or prevention of cartilage damage and/or arthritis and is capable of exhibiting effects of the regeneration of cartilage tissue, the inhibition of the expression of cartilage tissue matrix degrading enzyme and/or the inhibition of cartilage tissue ossification.

8 Claims, 11 Drawing Sheets

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 1

Glu Leu His Leu Asp
 1               5

<210> SEQ ID NO 2
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 2

Glu Leu His Leu Glu
 1               5

<210> SEQ ID NO 3
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 3

Glu Leu Lys Leu Asp
 1               5

<210> SEQ ID NO 4
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 4

Glu Leu Lys Leu Glu
 1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 5

Glu Leu Arg Leu Asp
 1               5

<210> SEQ ID NO 6
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 6

Glu Leu Arg Leu Glu
 1               5

<210> SEQ ID NO 7
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 7

Asp Leu His Leu Asp
 1               5

<210> SEQ ID NO 8
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 8

Asp Leu His Leu Glu
 1               5

<210> SEQ ID NO 9
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 9

Asp Leu Lys Leu Asp
 1               5
```

```
<210> SEQ ID NO 10
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 10

Asp Leu Lys Leu Glu
 1               5

<210> SEQ ID NO 11
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 11

Asp Leu Arg Leu Asp
 1               5

<210> SEQ ID NO 12
<211> LENGTH: 5
<212> TYPE: PRT
<213> ORGANISM: Artificial Sequence
<220> FEATURE:
<223> OTHER INFORMATION: Artificial peptide sequence prepared by
      coupling amino acid units one by one from the C-terminal, by Fmoc
      SPPS (9-flourenlymethyloxycarbonyl solid phase peptide synthesis)
      using an automated peptide synthesizer.

<400> SEQUENCE: 12

Asp Leu Arg Leu Glu
 1               5

<210> SEQ ID NO 13
<211> LENGTH: 20
<212> TYPE: DNA
<213> ORGANISM: Artificial Sequence
<220> FEATURE:
<223> OTHER INFORMATION: forward primer for Type II collagen

<400> SEQUENCE: 13
caggaccaaa gggacagaaa                                                20

<210> SEQ ID NO 14
<211> LENGTH: 20
<212> TYPE: DNA
<213> ORGANISM: Artificial Sequence
<220> FEATURE:
<223> OTHER INFORMATION: reverse primer for Type II collagen

<400> SEQUENCE: 14
ggttgccttg aaatccttga                                                20

<210> SEQ ID NO 15
<211> LENGTH: 20
<212> TYPE: DNA
<213> ORGANISM: Artificial Sequence
<220> FEATURE:
<223> OTHER INFORMATION: forward primer for MMP13
```

```
<400> SEQUENCE: 15
atggaccctc tggtctgttg                                          20

<210> SEQ ID NO 16
<211> LENGTH: 20
<212> TYPE: DNA
<213> ORGANISM: Artificial Sequence
<220> FEATURE:
<223> OTHER INFORMATION: reverse primer for MMP13

<400> SEQUENCE: 16
cgtgttttgg aaatcccagt                                          20

<210> SEQ ID NO 17
<211> LENGTH: 20
<212> TYPE: DNA
<213> ORGANISM: Artificial Sequence
<220> FEATURE:
<223> OTHER INFORMATION: forward primer for Type X collagen

<400> SEQUENCE: 17
cagtcaaggg ccttaatgga                                          20

<210> SEQ ID NO 18
<211> LENGTH: 20
<212> TYPE: DNA
<213> ORGANISM: Artificial Sequence
<220> FEATURE:
<223> OTHER INFORMATION: reverse primer for Type X collagen

<400> SEQUENCE: 18
cctgaagcct gatccaggta                                          20

<210> SEQ ID NO 19
<211> LENGTH: 20
<212> TYPE: DNA
<213> ORGANISM: Artificial Sequence
<220> FEATURE:
<223> OTHER INFORMATION: forward primer for GAPDH

<400> SEQUENCE: 19
acccagaaga ctgtggatgg                                          20

<210> SEQ ID NO 20
<211> LENGTH: 20
<212> TYPE: DNA
<213> ORGANISM: Artificial Sequence
<220> FEATURE:
<223> OTHER INFORMATION: reverse primer for GAPDH

<400> SEQUENCE: 20
cccagcatcg aaggtagaag                                          20
```

PEPTIDE AND USE THEREOF

TECHNICAL FIELD

The present invention relates to a novel peptide. Specifically, the present invention relates to a novel peptide which is effective for the treatment and/or prevention of cartilage damage or arthritis.

BACKGROUND ART

Cartilage tissue is composed of a matrix and chondrocytes. Among these, collagen fibers (collagen, proteoglycan) of the matrix, together with noncollagenous proteins, absorb and discharge water into/from cartilage to thereby play an important role in maintenance of physical properties unique to the cartilage. Damage of cartilage tissue is largely observed in joint diseases, and cartilage tissue of joints is broadly subdivided into four zones, that is, the outermost superficial tangential zone, a middle zone, a deep zone and a calcified zone (Clouet J et al., *Drug Discovery Today* (2009) 14:19/20, 913-925). The superficial tangential zone is a region with a relatively low proportion of the matrix, in which collagen fibers are densely arranged along the joint surface and chondrocytes having thin and flat cellular morphology are present, and which absorbs shearing force of articular movement. The middle zone is thicker than the superficial tangential zone, is composed of thick collagen fibers and spherical chondrocytes, and serves to withstand a load, due to having a high proportion of the matrix containing proteoglycan and water. The deep zone is rich in proteoglycan and noncollagenous proteins in conjunction with the highest content of matrix components but the lowest water content, and serves to impart the stability of tissue through vertical arrangement of relatively small numbers of chondrocytes close to the spherical shape and collagen fibers. The calcified zone has a specific structure known as tidemark and functions to fix cartilage tissue to bone tissue.

Damage of cartilage tissue constituting joints results in the onset of arthritis which is accompanied by swelling, warmth and pain. The onset of arthritis is irrespective of races and is classified into approximately 100 types depending on the pathogenic cause thereof. The most common form of arthritis is osteoarthritis, a degenerative joint disease which primarily caused by aging. Other examples of arthritis include rheumatoid arthritis and psoriatic arthritis which are autoimmune diseases, and septic arthritis caused by infections. In particular, degenerative arthritis is a representative disease of advanced age groups, and aging of joints is mainly responsible for the pathogenesis of degenerative arthritis. Further, since the incidence of degenerative arthritis is also due to a combined interaction of various factors, such as genetic factors, imbalanced nutrition, a lack of exercise, immoderate exercise or injury, behavior of applying a heavy load to joints, for example, overwork or habitual bad posture, and overload due to obesity, degenerative arthritis is also a disease with high frequency observed among young people (Gegout P P et al., *Joint Bone Spine* (2008) 669-671).

Weakening of joint-supporting tissue due to trauma or degenerative alteration leads to injury of cartilage tissue which serves to absorb impact, thus increasing bone-to-bone friction to cause pain and inflammation. Inflammation accelerates the formation of osteophytes around joints, which restricts mobility of joints and causes more severe pain.

Arthritis is a disease with a high pathogenic incidence among broad age groups and damaged tissue does not readily undergo spontaneous regeneration or restoration. Therefore, arthritis is responsible for long-term restriction of social activity of patients and deterioration of a quality of a patient's life.

Currently available therapeutic measures are broadly divided into conservative therapies such as exercise therapy including weight control, dietetic therapy, injection therapy and pharmacotherapy; and surgical therapies such as tissue regeneration using growth factors, implantation using artificially cultured cells, and artificial joint replacement which is applied when joints are severely damaged (Clouet J et al., *Drug Discovery Today* (2009) 14:19/20, 913-925).

Exercise therapy within the range of applying no heavy load to joints has an effect of strengthening the joint's surrounding tissue to retard further symptomatic aggravation, but provides no fundamental regeneration of damaged tissue and has difficulty of being carried out due to pain when the condition of illness is severe.

For the purpose of promoting tissue regeneration of joints or relieving inflammation, there have been used glucosamine or chondroitin which is a constituent component of cartilage, fish oil having an anti-inflammatory action, and other herbal pharmaceutical compositions (Derfoul A et al., *Osteoarthritis Cartilage* (2007) 15, 646-655; Tiraloche G et al., *Arthritis Rheum.* (2005) 52, 1118-1128; McAlindon T E et al., JAMA (2000) 283 (11): 1469-147; and Zainal Z et al., *Osteoarthritis Cartilage* (2009) 17(7): 896-905).

Further, a method of injecting hyaluronic acid (HA) which is a joint synovial fluid component has also been used for the relief of pain and prevention of symptomatic aggravation by reducing friction of damaged regions (Waddell D D et al., *Arthroscopy* (2010) 26(1):105-11; and Wang C T et al., *J. Bone Joint Surg. Am.* (2004) 86-A 538-545).

Although some of these conservative therapies have been reported to have beneficial therapeutic effects, their pain relief or therapeutic effects are insignificant or the mechanism thereof is not fully understood. Therefore, there is a need for further inspection from the viewpoint of therapeutic applications of such therapies (McAlindon T E et al., JAMA (2000) 283 (11): 1469-147).

For the relief of inflammation or pain, aspirin, acetaminophen, or various nonsteroidal antiinflammatory drugs (NSAIDs) and steroidal drugs such as cortisone have been used. However, these pharmacotherapies are not fundamental therapies which are capable of achieving the restoration of damaged tissue. In addition, long-term administration of such drugs has reportedly adverse side effects such as gastrointestinal, tissue or bone damage (Clouet J et al., *Drug Discovery Today* (2009) 14:19/20, 913-925; Glass G G *Dis. Mon.* (2006) 343-362; Zhang W et al., *Ann. Rheum. Dis.* (2004) 63, 901-907); Frampton J E et al., *Drugs* (2007) 67(16):2433-72; and McDonough A L. *Phys Ther.* (1982) 62(6): 835-9.).

For the purpose of regeneration or restoration of damaged cartilage tissue, use of a composition containing apigenin, or a growth factor or a portion thereof, such as FGF, BMPs (BMP7/OP-1) or TGFβ1, has been contemplated (Clouet J et al., *Drug Discovery Today* (2009) 14:19/20, 913-925; Shi S et al., *J. Biol. Chem.* (2009) 284 (1): 6697-6704; and Moore E E et al., *Osteoarthritis Cartilage* (2005) 13, 623-631). However, since there is limitation to carry out direct and repeated infusion with a growth factor composed of high molecular weight protein into arthritis patients, the practical application of such a growth factor to patients requires further investigation for a delivery method thereof.

When the above-mentioned conservative therapies provide no therapeutic effects or intense pain continues, a surgical therapy involving replacement of damaged joints with artificial joints is used. However, an artificial joint has a limited lifespan of about 10 years, so re-surgery is necessary where appropriate. In this case, re-surgery has limitations due to difficulty in removal of artificial joints stenosed to bone, a need for implantation of larger artificial joints, and a need for more extensive peripheral bone tissue. For these problems, the application of artificial joint replacement to younger people should be made with more care.

With the advancement of artificial cell culture techniques, it has recently been reported methods including artificial culture of chondrocytes from multipotent stem cells or autologous mesenchymal stem cells and implantation of the cultured chondrocytes (Csaki C et al., *Ann Anat.* (2008) 190(5): 395-412). Unfortunately, the chondrocyte implantation still has a large number of problems to be solved, in terms of being not easy to obtain a sufficient number of autologous cells, in conjunction with technical and cost problems associated with application thereof to numbers of patients, such as adhesion of implanted cells, regeneration efficiency and safety.

As we enter an aging society, the advanced age population suffering from arthritis is steadily increasing. Further, the incidence of joint diseases due to immoderate exercise, imbalanced nutrition, obesity or the like is also increasing among younger age groups. In order to reduce consequent economic loss and social expenses and improve life quality of the advanced age population, there is an urgent need for the development of an advanced anti-arthritis drug, which is capable of achieving more convenient, safe and fundamental regeneration and restoration of arthritis-damaged cartilage tissue, instead of conventional conservative dietetic therapy or pharmacotherapy to relieve inflammation or pain, surgical therapy such as artificial joint replacement, or implantation of artificially cultured chondrocytes.

DISCLOSURE

Technical Problem

The present invention is intended to provide a novel peptide or a pharmaceutically acceptable salt thereof.

Further, the present invention is intended to provide a composition for the treatment and/or prevention of at least one selected from cartilage damage and arthritis.

Further, the present invention is intended to provide a composition which is therapeutically effective for cartilage damage or arthritis.

Technical Solution

The present invention provides a peptide represented by formula (I):

$$X_1\text{-Leu-}X_2\text{-Leu-}X_3 \quad (I):$$

wherein $X_1$ represents Glu or Asp, $X_2$ represents His, Lys or Arg, $X_3$ represents Asp or Glu, with Glu, Asp, Leu, His, Lys and Arg being respectively glutamic acid, aspartic acid, leucine, histidine, lysine and arginine; or a pharmaceutically acceptable salt thereof.

The peptide is preferably a peptide (SEQ ID NO: 1; Glu-Leu-His-Leu-Asp) wherein $X_1$ represents Glu, $X_2$ represents His, and $X_3$ represents Asp.

Amino acids are classified depending on the attribute of R group (a variable group other than a carboxyl group, an amino group and a hydrogen atom attached in common to amino acids). Glu or Asp is classified as an acidic amino acid Negatively Charged (Acidic) R Groups, and His, Lys or Arg is classified as a basic amino acid Positively Charged (Basic) R Groups. The acidic amino acid has an R group which is negatively charged at pH 7.0 and also has one carboxyl group. The basic amino acid has an R group which is positively charged at pH 7.0. Amino acids belonging to the same classification have similar properties.

Each of constituent amino acids of the peptide may be in the L-form, D-form, and/or DL-form, all of which are encompassed in the constituent amino acids of the peptide of the present invention.

Examples of the pharmaceutically acceptable salt include hydrochloride, sulfate, phosphate, lactate, maleate, fumarate, oxalate, methanesulfonate, and p-toluenesulfonate.

Further, the present invention provides a use of the peptide of the present invention or a pharmaceutically acceptable salt thereof, for the treatment and/or prevention of cartilage damage or arthritis.

Therefore, the present invention provides a composition, containing the peptide of the present invention or a pharmaceutically acceptable salt thereof as an active ingredient, for the treatment and/or prevention of at least one selected from cartilage damage and arthritis.

The "treatment and/or prevention" may be by at least one selected from the regeneration of cartilage tissue, the inhibition of the expression of cartilage tissue matrix degrading enzyme and the inhibition of cartilage tissue ossification, and the arthritis is preferably a joint disease which is accompanied by degeneration of cartilage and subchondral bone.

Further, the present invention provides a composition containing the peptide of the present invention or a pharmaceutically acceptable salt thereof and a transforming growth factor beta 1 (TGFβ1).

The ratio of the peptide or a pharmaceutically acceptable salt thereof and TGFβ1 in the composition may be in a range of 1:20 to 40 by weight.

The composition of the present invention may be a pharmaceutical composition which may be formulated with the addition of a pharmaceutically acceptable carrier.

The peptide of the present invention can be prepared by processes commonly used in peptide synthesis. For example, the peptide can be prepared by those processes described in Schroder and Lubke, The Peptides, Vol. 1, Academic Press, New York, 1965, and the like, and can be prepared by either solution-phase synthesis or solid-phase synthesis.

Examples of the methods for formation of the peptide bonds include azide method, acid chloride method, symmetrical anhydride method, mixed anhydride method, carbodiimide method, carbodiimide-additive method, activated ester method, carbodiimidazole method, oxidation-reduction method, and the method employing Woodward reagent K.

Before carrying out the coupling reaction, a carboxyl group, an amino group, and the like which do not participate in the reaction may be protected, and the carboxyl group and amino group which participate in the coupling reaction may be activated by methods known in the art.

Examples of the protecting groups for a carboxyl group include ester-forming groups such as methyl, ethyl, benzyl, p-nitrobenzyl, t-butyl and cyclohexyl.

Examples of the protecting groups for an amino group include benzyloxycarbonyl, t-butoxycarbonyl, isobornyloxycarbonyl, and/or 9-fluorenylmethyloxycarbonyl.

Examples of the activated forms of a carboxyl group include symmetrical anhydride, azide and active ester (ester with alcohol, e.g., pentachlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide or 1-hydroxybenzotriazole).

An example of the activated amino group is amide phosphate.

The reaction is carried out in a solvent such as chloroform, dichloromethane, ethyl acetate, N,N-dimethylformamide, dimethyl sulfoxide, pyridine, dioxane, tetrahydrofuran, water, methanol or a mixture thereof.

The reaction temperature may be in the range of approx. −30 to 50° C. which is generally employed for the reaction.

The reaction for removing the protecting group of the peptide may vary depending on the kind of the protecting group, but it should be one which is able to release the protecting group without giving any influence to the peptide bonding.

The protecting group can be removed by acid treatment, for example, treatment with hydrogen chloride, hydrogen bromide, hydrogen fluoride, methanesulfonic acid, trifluoromethanesulfonic acid, trifluoroacetic acid or a mixture of these acids. Further, reduction with a sodium metal in liquid ammonia or catalytic reduction over palladium-carbon may be employed.

Upon carrying out the reaction of removing the protecting group by the acid treatment, an additive such as anisole, phenol or thioanisole may be adopted.

After the reaction is completed, the prepared peptide of the present invention can be recovered by a conventional process for purification of peptides, for example, extraction, partitioning, reprecipitation, recrystallization or column chromatography.

Further, the peptide of the present invention can be converted into a variant or pharmaceutically acceptable salt thereof by using a conventional method.

The peptide in accordance with the present invention may be synthesized by an automated peptide synthesizer or may be produced by genetic engineering techniques. For example, a desired peptide can be produced by preparing a fusion gene encoding a fusion protein consisting of a fusion partner and the peptide of the present invention through gene manipulation, transforming a host microorganism with the fusion gene, expressing a desired peptide in the form of a fusion protein in the host microorganism, and then cleaving and separating the peptide of the present invention from the fusion protein using a protease or compound.

A dose of the peptide or a pharmaceutically acceptable salt thereof is in the range of 150 μg/day to 1 mg/day, preferably 0.5 mg/day to 1 mg/day for parenteral administration. For oral administration, the dose is 1.2 to 1.5 times larger than the parenteral dose.

The peptide or composition of the present invention is administered largely by parenteral routes, for example local injection (intra-articular cavity injection), intravenous or subcutaneous injection, or transnasal administration. Further, oral administration may be adopted, if necessary.

The peptide of the present invention or a pharmaceutically acceptable salt thereof or the composition of the present invention, in combination with a pharmaceutically acceptable carrier, can be formulated into desired dosage forms such as injections, powders, nasal drops, granules, or tablets.

The pharmaceutically acceptable carrier can be prepared according to a number of factors well-known to those skilled in the art, for example, taking into consideration the following non-limiting factors: the particular physiologically active material to be used, and its concentration, stability and intended bioavailability; the disease, disorder or condition being treated; the subject being treated, and its age, size and general condition; and the composition's intended route of administration, for example, local, intravenous, intramuscular, transdermal, oral, or nasal. Generally, examples of the pharmaceutically acceptable carrier used for the administration of a physiologically active material, other than the oral administration route, may include D5W (5% glucose in water), an aqueous solution containing 5% by volume or less of dextrose, and physiological saline. In the case of local intralesional injection, a variety of injectable hydrogels may be employed to enhance therapeutic effects and increase the duration of drug efficacy. In addition, the pharmaceutically available carrier may contain additional ingredients that can enhance the stability of active ingredients, such as preservatives or antioxidants. The peptide or composition of the present invention may be preferably formulated into a desired dosage form, depending upon diseases to be treated and ingredients, using any appropriate method known in the art, for example, as disclosed in "Remington's Pharmaceutical Sciences," Mack Publishing Co., Easton, Pa. (latest edition).

The peptide of the present invention may be stored in a physiological saline solution and may be freeze-dried in an ampoule after addition of mannitol or sorbitol. The freeze-dried peptide may be dissolved in physiological saline or the like for reconstitution prior to use.

Further, the present invention provides a method for the treatment and/or prevention of cartilage damage or arthritis, including administering the peptide of the present invention or a pharmaceutically acceptable salt thereof to a mammal including a human in need thereof.

Further, the present invention provides a medicinal use of the peptide of the present invention or a pharmaceutically acceptable salt thereof, preferably for the treatment and/or prevention of cartilage damage or arthritis.

The details mentioned in the peptide of the present invention or a pharmaceutically acceptable salt thereof or the composition of the present invention shall apply to the use and the treatment and/or prevention method in accordance with the present invention as long as there is no contradiction therebetween.

Advantageous Effects

The peptide of the present invention or a pharmaceutically acceptable salt thereof is effective for the treatment and/or prevention of cartilage damage or arthritis, and can exhibit effects on the regeneration of cartilage tissue, the inhibition of the expression of cartilage tissue matrix degrading enzyme and/or the inhibition of cartilage tissue ossification.

MODE FOR INVENTION

Figure 1:
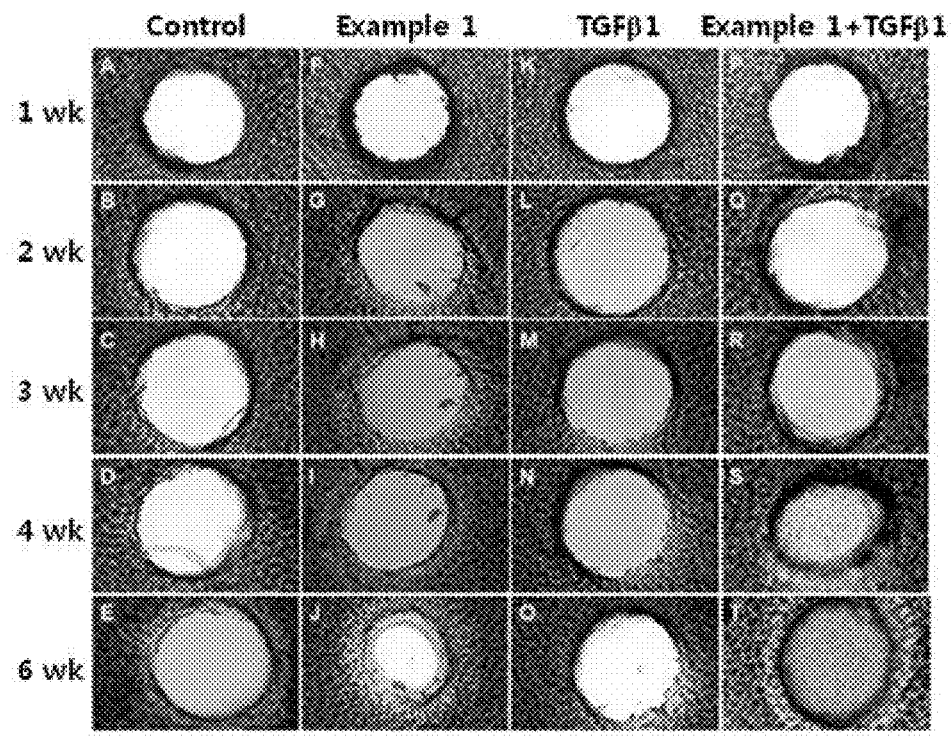
FIG. 1 illustrates a photograph showing changes in damaged cartilage tissue, in accordance with an embodiment of the present invention.

Now, the present invention will be described in more detail with reference to the following examples. These examples are provided only for illustrating the present invention and should not be construed as limiting the scope and spirit of the present invention.

EXAMPLE 1

Preparation of Peptide

A peptide (Glu-Leu-His-Leu-Asp: SEQ ID NO: 1) having an amino acid sequence of SEQ ID NO: 1 was prepared by Peptron Inc. (South Korea), at the request of the present inventors. Specifically, amino acid units were coupled one by one from the C-terminal, by Fmoc SPPS (9-fluorenylmethyloxycarbonyl solid phase peptide synthesis) using an automated peptide synthesizer (ASP48S, Peptron Inc.).

NH$_2$-His(Trt)-2-chloro-Trityl Resin was used in which the first amino acid of the C-terminal of the peptide was attached to a resin. All the amino acids used in the peptide synthesis were those protected by Trityl (Trt), t-butyloxycarbonyl (Boc), t-butyl (t-Bu), and the like, whereby the N-terminal is protected by Fmoc, and residues are all removed in acid. As a coupling reagent, 2-(1H-benzotriazol-1-yl)-1,1,3,3-tetramethyluronium hexafluorophosphate (HBTU)/hydroxybenzotriazole (HOBt)/N-methylmorpholine (NMM) was used. (1) Protected amino acid (8 equivalents) and the coupling reagent HBTU (8 equivalents)/HOBt (8 equivalents)/NMM (16 equivalents) were dissolved in dimethylformamide (DMF) and added followed by reaction at room temperature for 2 hours. (2) The removal of Fmoc was carried out by adding 20% piperidine in DMF, followed by reaction at room temperature for 5 minutes twice. Reactions of (1) and (2) were repeated to prepare a basic peptide backbone, and the peptide was separated from the resin using trifluoroacetic acid (TFA)/1,2-ethanedithiol (EDT)/thioanisole/triisopropylsilane (TIS)/H$_2$O=90/2.5/2.5/2.5/2.5. The peptide was purified by reverse phase HPLC using a Vydac Everest C18 column (250 mm×22 mm, 10 µm), and then separated by water-acetonitrile linear gradient (10 to 75% (v/v) of acetonitrile) containing 0.1% (v/v) trifluoroacetic acid. A molecular weight of the purified peptide was confirmed using an LC/MS (Agilent HP 1100 series), followed by freeze-drying.

EXAMPLES 2 to 12

Preparation of Peptides

Peptides of Examples 2 to 12 were prepared in the same manner as in Example 1, except that the amino acid sequences given in Table 1 below were used in place of the amino acid sequence of Example 1.

TABLE 1

| Example No. | Amino acid sequence | SEQ ID NO |
|---|---|---|
| Example 2 | Glu-Leu-His-Leu-Glu | 2 |
| Example 3 | Glu-Leu-Lys-Leu-Asp | 3 |
| Example 4 | Glu-Leu-Lys-Leu-Glu | 4 |
| Example 5 | Glu-Leu-Arg-Leu-Asp | 5 |
| Example 6 | Glu-Leu-Arg-Leu-Glu | 6 |
| Example 7 | Asp-Leu-His-Leu-Asp | 7 |
| Example 8 | Asp-Leu-His-Leu-Glu | 8 |
| Example 9 | Asp-Leu-Lys-Leu-Asp | 9 |
| Example 10 | Asp-Leu-Lys-Leu-Glu | 10 |
| Example 11 | Asp-Leu-Arg-Leu-Asp | 11 |
| Example 12 | Asp-Leu-Arg-Leu-Glu | 12 |

EXAMPLE 13

Confirmation of Cartilage Regeneration Effects Using Damaged Cartilage Tissue Explants Articular chondrocyte explants were prepared from hoof joints of less than 3-year old cows within one hour of being sacrificed at a regional slaughterhouse (located in Ojeong-dong, Daejeon, South Korea). For this purpose, a cartilage portion other than bone was uniformly cut off from the joint and sliced into a size of about 3 mm×3 mm using a surgical knife to prepare cartilage tissue explants. Using a syringe (21G) whose tip was truncated and ground, damaged regions were prepared by making vertical holes to the surface uniformly at the center of the explant.

The perforated tissue explants were divided into 4 groups including a control group. Individual groups were placed in Dulbecco's Modified Eagle Medium/F12 (DMEM/F12, 1:1, Welgene) supplemented with ascorbate (50 µg/ml, Sigma) and 10% fetal bovine serum (FBS, Invitrogen), and then treated with 25 µM of the peptide of Example 1, 2 ng/ml of a transforming growth factor beta 1 (TGF(31, Promokine), and a mixture of 25 µM of the peptide of Example 1 and 2 ng/ml of TGFβ1, respectively. The individual groups were divided again into two subgroups, followed by incubation for 1 or 6 weeks. For the 6-week-incubated group, the damaged region was weekly examined under a microscope, followed by taking a photograph. In addition, the 1-week-incubated tissue explant and the 6-week-incubated tissue explant were fixed, respectively, in a 3.7% formaldehyde/phosphate buffered saline(3.7% formaldehyde/PBS). Then, according to the experimental method of standard histochemistry, paraffin section slides were prepared, followed by hematoxylin & eosin (H&E) staining and microscopic examination of cell shape and distribution in terms of morphology. Collagen was subjected to Masson's trichrome staining, and the shape and distribution of cells in the tissue were examined under a microscope. For comparison, the control group was treated in the same manner as in the group treated with the peptide of Example 1, except that the peptide of Example 1 was not treated.

The results are shown in FIGS. 1 to 4.

FIG. 1 illustrates a micrograph of changes over time in cartilage tissue after treatment of articular chondrocyte explants with Example 1 or Example 1+TGFβ1.

As shown in FIG. 1, when Example 1 alone was treated, the damaged region was gradually decreased after 2 weeks, cells began to adhere around the damaged region after 4 weeks, and the damaged region was remarkably reduced after 6 weeks, thus demonstrating that the peptide of Example 1 exhibits the regeneration of the damaged region (FIGS. 1F to J). Further, when the peptide of Example 1 was treated in combination with TGFβ1, cells began to proliferate around the hole after 3 weeks, and the damaged region was completely filled with the cells after 6 weeks (FIGS. 1P to T). As compared to the treatment with the peptide of Example 1 alone, combined treatment of TGFβ1 with the peptide of Example 1 resulted in regeneration of the damaged region one week earlier, and cells previously appearing only around the hole at Week 3 had completely filled the damaged region at Week 4.

Figure 2:
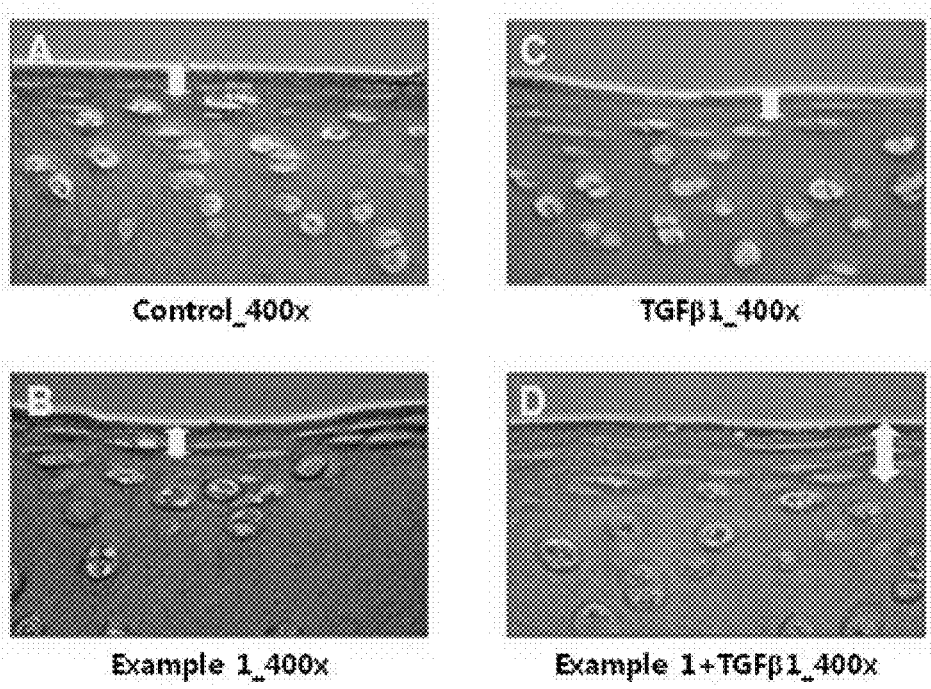
FIG. 2 illustrates the results of cartilage tissue regeneration effects observed with hematoxylin & eosin staining, in accordance with an embodiment of the present invention.
Figure 3:
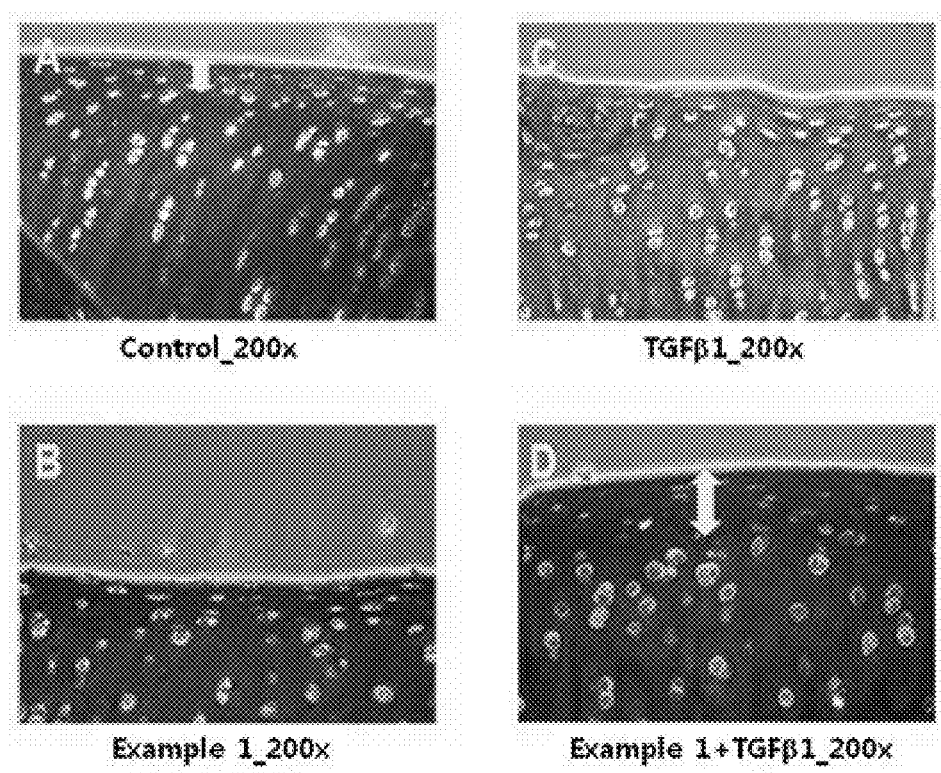
FIG. 3 illustrates the results of cartilage tissue regeneration effects observed with collagen staining, in accordance with an embodiment of the present invention.
Figure 4:
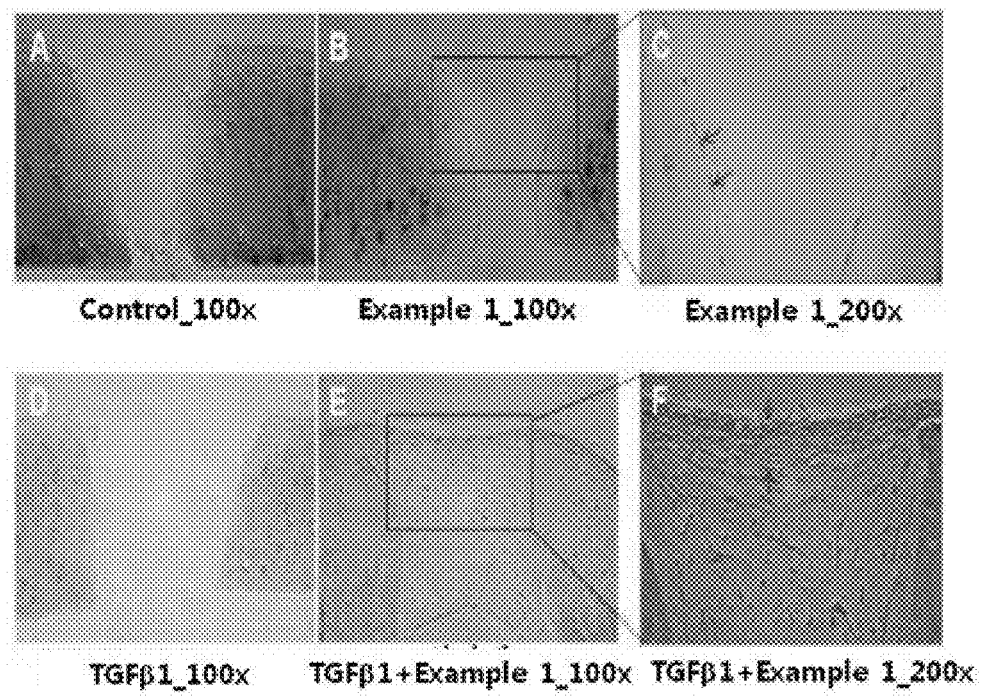
FIG. 4 illustrates the results of cartilage tissue regeneration effects observed with hematoxylin & eosin staining, in accordance with an embodiment of the present invention.

FIG. 2 illustrates the results of tissue regeneration effects observed with hematoxylin & eosin staining after one-week culturing of cartilage tissue explants treated with Example 1 or Example 1+TGFβ1, and FIG. 3 illustrates the results of collagen staining. FIG. 4 illustrates the results of tissue regeneration effects observed with hematoxylin & eosin staining after 6-week culturing of cartilage tissue explants treated with Example 1 or Example 1+TGFβ1. The arrow in FIG. 2 and FIG. 3 represents the superficial layer of the cartilage tissue explant. FIGS. 4C and 4F are each partially enlarged views of the square parts of FIGS. 4B and 4E, wherein the arrow represents the superficial layer of the cartilage tissue explant.

As shown in FIG. 2 and FIG. 3, combined treatment of the peptide of Example 1 and TGFβ1 resulted in a more than 2-fold increase in the superficial layer thickness of the cartilage tissue explant, as compared to the control group (FIG. 2D and FIG. 3D), and collagen staining was more intense, thus demonstrating that the peptide of Example 1 leads to an increase in the synthesis of collagen (FIG. 3D).

Further, as shown in FIG. 4, when the peptide of Example 1 was treated for 6 weeks, the damaged region was narrowed, and new cells were adhered around the damaged region (FIGS. 4B and 4C). When the peptide of Example 1 was treated in combination with TGFβ1, it can be seen that the cartilage tissue including the superficial layer (as indicated by the arrow in FIG. 4F) was regenerated to the original shape and the damaged region of the cartilage tissue explant was completely filled with the regenerated cartilage tissue (FIGS. 4E and 4F). On the other hand, the control group and the TGFβ1-alone treated group exhibited substantially no change in the damaged region of the explants (FIGS. 4A and 4D).

From these results, it can be seen that the peptide of Example 1 is capable of providing the regeneration of damaged cartilage by promoting attachment and proliferation of chondrocytes to/in the damaged region while increasing the synthesis of collagen which is a major matrix component, and it can also be seen that TGFβ1 further accelerates the regeneration speed of damaged cartilage. Further, it seems that the peptides of Examples 2 to 12, which are variants having an amino acid sequence similar to that of the peptide of Example 1, will exhibit similar effects.

EXAMPLE 14

Confirmation of Cartilage Regeneration Effects Using Articular Chondrocyte Pellet Effects of Peptide of Example 1 on Expression of Gene In order to ensure that cellular properties of articular chondrocytes are maintained similarly to those of biological tissue, the cells were pelleted and cultured.

Cartilage tissue was prepared from hoof joints of less than 3-year old cows within one hour of being sacrificed at a regional slaughterhouse (located in Ojeong-dong, Daejeon, South Korea). For this purpose, a cartilage portion other than bone was cut using a surgical knife and collected to use. The cartilage tissue was sliced into a hexahedron of about 1 mm long at each side and placed in DMEM/F12 (Welgene) supplemented with Pronase (1 mg/ml, Roche), followed by reaction in a 5% $CO_2$ incubator at 37° C. for 1.5 hours. The Pronase-treated tissue was washed twice with PBS(phosphate buffered saline) and then once with DMEM/F12. The washed cartilage tissue was placed in DMEM/F12 supplemented with 5% FBS (fetal bovine serum) (Invitrogen), Collagenase P (0.25 mg/ml, Roche) and DNase I (20 μg/ml, Sigma) and was allowed to react in a 5% $CO_2$ incubator at 37° C. for 8 to 12 hours, such that the tissue was completely degraded. After the degradation was completed, the cells were collected by centrifugation at 500 xg for 15 minutes and washed twice with PBS. The cells were suspended at a cell density of $2 \times 10^6$ cells/ml in DMEM/F12 supplemented with 10% FBS and ascorbate (50 μg/ml, Sigma), and 1ml/tube of the cells were dispensed into 15 ml conical tubes. The cells were pelleted by centrifugation at 500 xg for 10 minutes and cultured in a 5% $CO_2$ incubator at 37° C. for 2 days, thereby preparing a cell pellet which is solid. The pellet was transferred to a 24-well plate and cultured for 5 days. Thereafter, the pellet was treated with dimethyl sulfoxide (DMSO), 2 ng/ml of transforming growth factor beta 1 (TGFβ1, Promokine), a mixture of 25 μM of the peptide of Example 1 and 2 ng/ml of TGFβ1, and 25 μM of the peptide of Example 1, respectively, followed by culture for another 5 days. On Day 13, the cells were cultured in serum-free media for 24 hours. On Day 14, the cells were cultured for 24 hours in serum-free media supplemented with 2 ng/ml of TGFβ1, a mixture of 25 μM of the peptide of Example 1 and 2 ng/ml of TGFβ1, or 25 μM of the peptide of Example 1, respectively.

RNA was isolated from the cultured pellet using TRIZOL (Invitrogen) and quantified by absorbance at 260 nm. cDNA was synthesized from 2.25 μg of RNA, using a random hexamer and 5x Reverse Transcriptase Master premix (Elpis Biotech, South Korea). Using 1 μl of synthesized cDNA, amplification was carried out by polymerase chain reaction (PCR) to investigate expression levels of genes. The genes to be investigated are as follows: a gene for chondrocyte-characteristic type II collagen (COL2A1) as a gene for confirming the regeneration of articular cartilage tissue; a gene for matrix metallopeptidase 13 (MMP13) which is over-expressed in damaged cartilage tissue and is involved in the degradation of the matrix, as a gene for confirming whether or not it is capable of preventing additional cartilage damage; and a gene for type X collagen (COL10A1) characteristic to hypertrophic chondrocytes involved in the ossification of articular tissue, as a gene for confirming whether or not it is over-activated and progressed to ossification.

Sequences of PCR primers used for the amplification of individual genes and the size of PCR products are as follows.

```
Type II collagen (product size: 381 bp)
Forward primer:
                                    (SEQ ID NO: 13)
5'-CAGGACCAAAGGGACAGAAA-3'

Reverse primer:
                                    (SEQ ID NO: 14)
5'-GGTTGCCTTGAAATCCTTGA-3'
```

-continued

MMP13 (product size: 600 bp)
Forward primer:
(SEQ ID NO: 15)
5'-ATGGACCCTCTGGTCTGTTG-3'

Reverse primer:
(SEQ ID NO: 16)
5'-CGTGTTTTGGAAATCCCAGT-3'

Type X collagen (product size: 454 bp)
Forward primer:
(SEQ ID NO: 17)
5'-CAGTCAAGGGCCTTAATGGA-3'

Reverse primer:
(SEQ ID NO: 18)
5'-CCTGAAGCCTGATCCAGGTA-3'

Glyceraldehyde-3-phosphate dehydrogenase
(GAPDH) (product size: 345 bp)
Forward primer:
(SEQ ID NO: 19)
5'-ACCCAGAAGACTGTGGATGG-3'

Reverse primer:
(SEQ ID NO: 20)
5'-CCCAGCATCGAAGGTAGAAG-3'

Specifically, PCR was carried out under the following reaction conditions. The PCR reaction employed 1 μl of cDNA, 10 μl of 2× Taq polymerase master mix (Solgent), 0.5 μl of each primer set (10 pmole/μl), and 8 μl of distilled water. PCR amplification consisted of denaturation at 94° C. for 2 minutes, followed by reaction at 94° C. for 30 seconds, at 58° C. for 45 seconds and at 72° C. or 1 minute, with 32 cycles for Type II collagen, Type X collagen and MMP13, and 26 cycles for GAPDH, respectively. PCR amplification products were subjected to electrophoresis on 1% agarose gel and stained with ethidium bromide (EtBr, μg/ml) for 15 minutes, followed by confirmation on UV light. Using an image processing program, Image J (NIH), expression levels of individual genes were normalized to GAPDH expression level, and then relative expression levels were compared therebetween.

Figure 5:
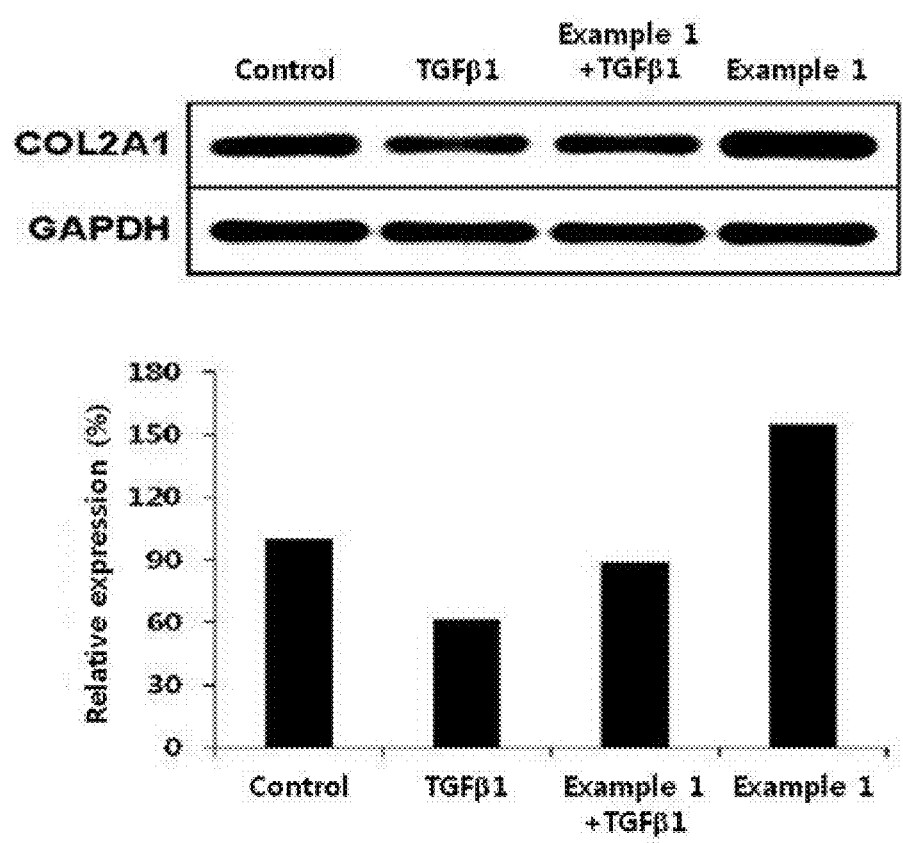
FIG. 5 illustrates the results of changes in the gene expression of type II collagen in cultured cartilage tissue cells, in accordance with an embodiment of the present invention.
Figure 6:
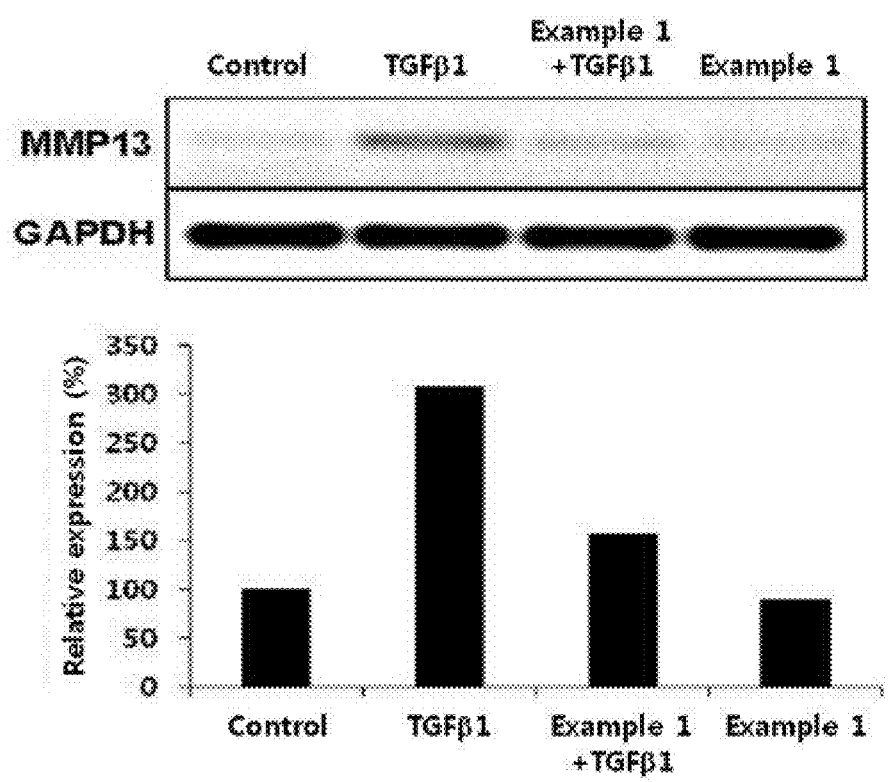
FIG. 6 illustrates the results of changes in the gene expression of MMP13 in cultured cartilage tissue cells, in accordance with an embodiment of the present invention.
Figure 7:
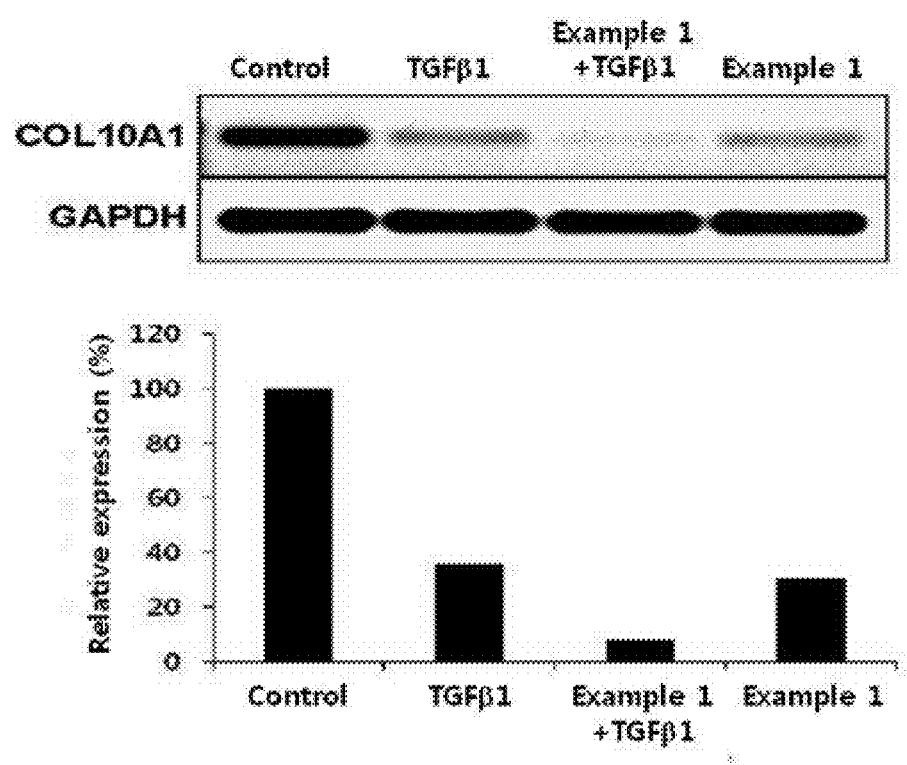
FIG. 7 illustrates the results of changes in the gene expression of type X collagen in cultured cartilage tissue cells, in accordance with an embodiment of the present invention.

The results are shown in FIG. 5 to FIG. 7. FIG. 5 illustrates the results showing changes in the expression of type II collagen (COL2A1) upon treatment of articular chondrocyte cells with the peptide of Example 1. FIG. 6 illustrates the results showing changes in the expression of MMP13. FIG. 7 illustrates the results showing changes in the expression of type X collagen (COL10A1). In each of FIG. 5 to FIG. 7, the upper column is an electrophoretic photograph of PCR amplification products on 1% agarose gel, and the lower column is a quantitative graph of electrophoretic bands using an image processing program Image J (NIH). In the graph, the y-axis represents % value of the relative band intensity of Example samples compared to the control group, when the band intensity of the control group is taken to be 100%.

As shown in FIG. 5 to FIG. 7, the peptide of Example 1 resulted in a 55% increase in the expression of type II collagen which is connected with the regeneration of cartilage tissue, as compared to the control group. Combined treatment of the peptide of Example 1 with TGFβ1 resulted in a 27% increase in the expression of type II collagen, as compared to the TGFβ1 alone-treated group (FIG. 5). In addition, the peptide of Example 1 resulted in a 10% decrease in the expression of matrix metallopeptidase 13 (MMP13) which is involved in the degradation of the matrix of cartilage tissue, as compared to the control group. Combined treatment of the peptide of Example 1 with TGFβ1 resulted in a 150% decrease in the expression of MMP13, as compared to the TGFβ1-treated group (FIG. 6). The peptide of Example 1 resulted in a 69% decrease in the expression of type X collagen (COL10A1) characteristic to hypertrophic chondrocytes involved in the ossification of articular tissue due to over-activation thereof, as compared to the control group. Combined treatment of the peptide of Example 1 with TGFβ1 resulted in a 78% decrease in the expression of COL10A1, as compared to the TGFβ1-treated group (FIG. 7).

From these results, it was demonstrated that the peptide of Example 1 activates chondrocytes of articular tissue to promote the synthesis of major matrix proteins constituting cartilage, and inhibits the expression of a major matrix degrading enzyme, thereby effectively promoting the regeneration of damaged articular cartilage tissue. Further, despite the fact that the peptide of Example 1 promotes the activation of chondrocyte, the peptide of Example 1 inhibits the differentiation into hypertrophic chondrocytes which may be progressed to ossification of articular tissue (osteophyte formation) and therefore has an effect of facilitating the regeneration of damaged tissue into normal tissue.

Effects of Peptides of Examples 2 to 12 on Expression of Genes

Effects of peptides were evaluated in the same manner as in Section "Effects of peptide of Example 1 on expression of genes", except that peptides of Examples 2 to 12 were respectively used in place of the peptide of Example 1. Table 2 below shows the experimental results for effects of the peptides of Examples 1 to 12 on the expression of type II collagen in cartilage chondrocyte cells.

TABLE 2

| Sample | Relative expression of Type II collagen (%) (Mean ± SD) |
|---|---|
| None | 100 ± 10 |
| Example 1 | 155 ± 12 |
| Example 2 | 163 ± 19 |
| Example 3 | 161 ± 29 |
| Example 4 | 124 ± 12 |
| Example 5 | 149 ± 27 |
| Example 6 | 158 ± 38 |
| Example 7 | 190 ± 38 |
| Example 8 | 115 ± 42 |
| Example 9 | 147 ± 41 |
| Example 10 | 166 ± 26 |
| Example 11 | 157 ± 34 |
| Example 12 | 159 ± 28 |

Table 2 shows the comparison results of changes in the expression of type II collagen in cartilage tissue culture cells, between the peptides of Examples 2 to 12 which are variants having an amino acid sequence similar to that of the peptide of Example 1. For reference, the results are also provided for no treatment. Numerical values in Table 2 are given as mean-standard deviation and the number of samples is 3 for each group. Data were calculated using a statistical program PASW Statistics (ver. 17.0, SPSS Inc.). Mean±standard deviation was given at a level of $p<0.05$ by using one-way analysis of variance, and significance between mean values of experimental groups was tested by least significant difference (LSD). Similar to Example 1, Examples 2 to 12 also exhibited a significant increase in the expression of type II collagen, as compared to the non-treated group. As a consequence, it was demonstrated that the peptides of Examples 2 to 12, which are amino acid sequence variants of Example 1, also exhibit effects similar to that of the peptide of Example 1 on the expression of type II collagen which is major extracellular matrix (ECM) component of cartilage (Table 2). Accordingly, it can be seen that all the peptides of Examples 1 to 12 exhibit cartilage regeneration effects.

EXAMPLE 15

Cartilage Regeneration Effects of Peptide Compounds in Degenerative Arthritis Model As experimental animals, 18 to 22-week-old male New Zealand white rabbits (n=10), weighing 3 to 3.5 kg, were purchased from Orient Bio Inc. (South Korea). The animal experiments were performed in accordance with guidelines of the Institute of Laboratory Animal Resources (ILAR) under approval of Institutional Animal Care and Use Committee of Samsung Biomedical Research Institute (SBRI, Seoul, South Korea). Degeneration of articular cartilage was induced by surgically dissecting the patellar anterior cruciate ligament of rabbits and breeding the animals in a cage for 4 weeks. The animals were divided into a control group and an experimental group.

The rabbits were put under general anesthesia by intramuscularly injecting 2.5 mg/kg of xylazine (Rompun, Bayer) and 8 mg/kg of Tiletamine/Zolazepam (Zoletil, Virbac). Then, the patellar joints of right hind legs of animals were shaved and disinfected. Patellar skins and joint capsules were excised and patellae were displaced to expose anterior cruciate ligaments. Thereafter, the ligament was excised using a razor blade (No. 11) and the joint capsule and skin were sutured. After the surgical operation was completed, the rabbits were raised in a cage for 4 weeks while allowing for routine motion. The animals were housed under the following conditions: temperature of 20 to 25° C. humidity of 10% to 50%, and Light/Dark (L/D) cycle: (light from 08:00 a.m. to 20:00 p.m.). All animals were fed once a day. At Week 4 after the surgical operation, the rabbits were divided into two groups, followed by intra-articular cavity injection. The control group was given an injection of a vehicle (5% lactose/physiological saline). For the experimental group, 200 µl of 52.5 µM peptide solution was injected to the group to which 30 µM of the peptide of Example 1 was administered, and 200 µl of 157.5 µM peptide solution was injected to the group to which 90 µM of the peptide of Example 1 was administered. The above-mentioned peptide was prepared in a solvent of 5% lactose/physiological saline prior to use. An injection was given once a week for 4 weeks. 1 and 5 weeks after the final injection (Week 8 and 12 after the first operation), the experimental animals were euthanized by vascular injection of 1 to 2 mM/kg of KCl under deep anesthesia.

The proximal portion (femoral region) of the patellar articular bone was excised. For the comparison with normal tissue, left normal articular region was also additionally excised, followed by naked-eye examination and photographing. The excised articular regions were fixed in 10% formalin, decalcified by using a decalcifier solution (Calci-Clear Rapid, National Diagnostics), and then made into paraffin blocks. The frontal plane of articular bone was cut into a thickness of 4 µm, thereby preparing a slide. In order to examine the structure and distribution of cells, hematoxylin & eosin (H&E) staining was carried out. In order to examine the distribution of proteoglycan in the matrix, Safranin O staining was carried out. In order to examine the distribution of collagen, Masson's Trichrome staining was carried out. The H&E staining was carried out using Harris hematoxylin (Melrose J. et al., Spine (2002) 1756-1764) after the slide was consecutively dehydrated with xylene, and 100%, 90%, 70% ethanol for 10 minutes each time. The Safranin O staining was carried out by dehydration of the slide in the same manner as in H&E staining, staining of the slide in 0.02% Fast green for 3 minutes, 1% acetic acid for 30 seconds and 0.1% Safranin O for 5 minutes, and consecutive 10 times dipping and dehydration of the slide in 70%, 90%, 100% ethanol, and xylene. Masson's Trichrome staining was carried out using Trichrome (Melrose J. et al., Eur. Spine J. (2007) 2193-2205).

The slides were prepared according to a normal group, a control group (lactose-administered group), and an experimental group (group to which the peptide of Example 1 was administered) and were examined under a microscope.

Figure 8:
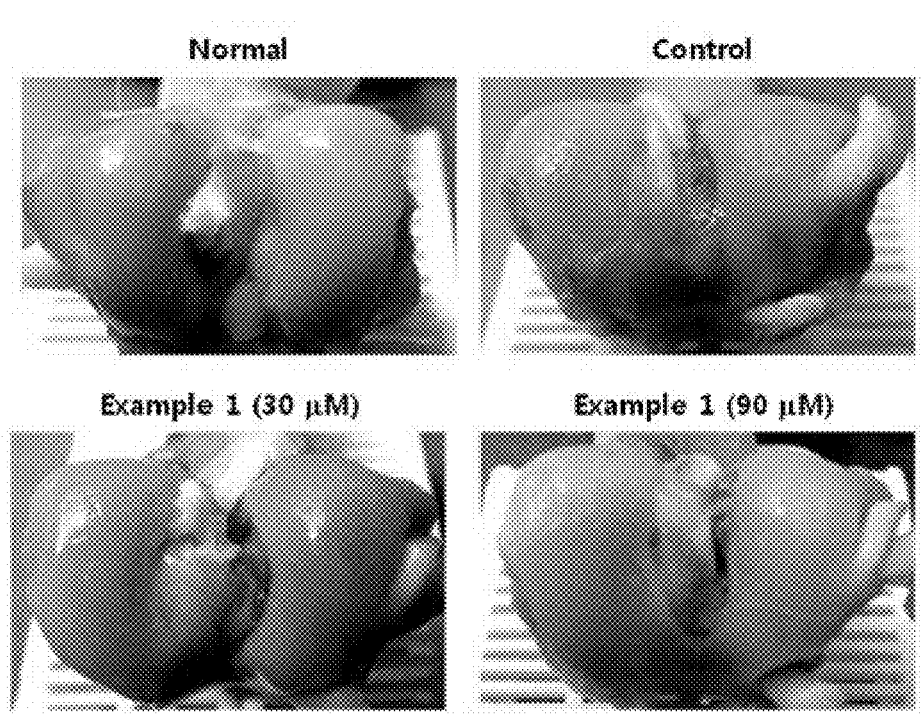
FIG. 8 illustrates a photograph showing the results of cartilage regeneration effects confirmed by visual observation in a degenerative arthritis model, in accordance with an embodiment of the present invention.

The results observed by naked eyes are shown in FIG. 8. As shown in FIG. 8, the articular cartilage tissue of the normal group was smooth and glossy, whereas the control group (lactose-administered group) of a degenerative osteoarthritis model exhibited a portion in which cartilage tissue was damaged and removed, and had a decreased gloss. On the other hand, the articular cartilage tissue of the experimental group (group to which the peptide of Example 1 was administered; 30 µM, 90 µM) exhibited a smooth surface and gloss close to the normal state, which results from the regeneration of damaged cartilage tissue.

Figure 9:
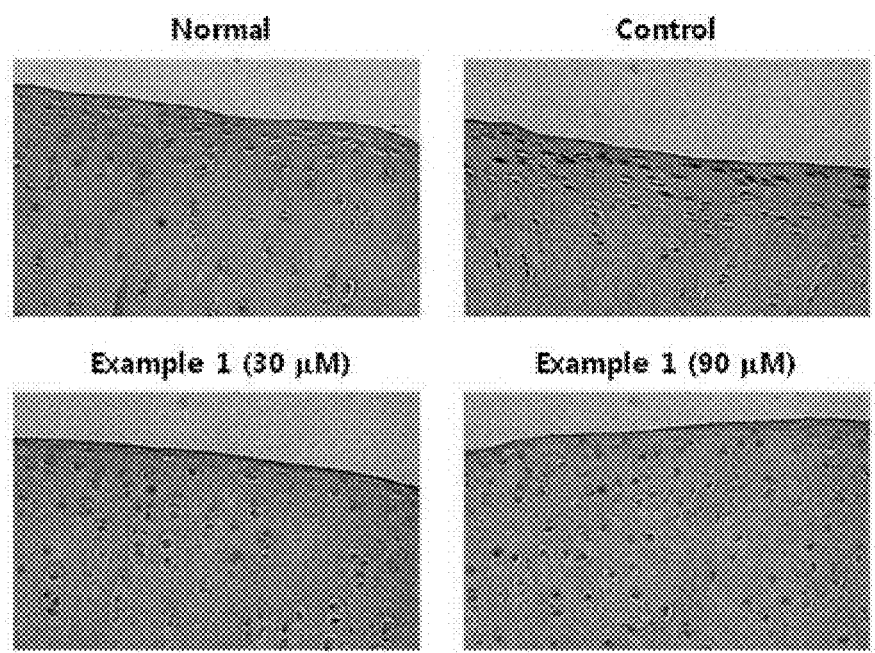
FIG. 9 illustrates the results of cartilage regeneration effects confirmed with hematoxylin & eosin staining in a degenerative arthritis model, in accordance with an embodiment of the present invention.

The H&E staining results are shown in FIG. 9. As shown in FIG. 9, only the control group (lactose-administered group) exhibited fibrochondrocytes (intense staining) on the superficial layer of cartilage tissue, whereas the experimental group (group to which the peptide of Example 1 was administered) exhibited a staining pattern similar to that of the normal group and showed an increased cell size due to the activation of cells. Therefore, it can be seen that the peptide of Example 1 activates articular chondrocytes in the experimental group.

Figure 10:
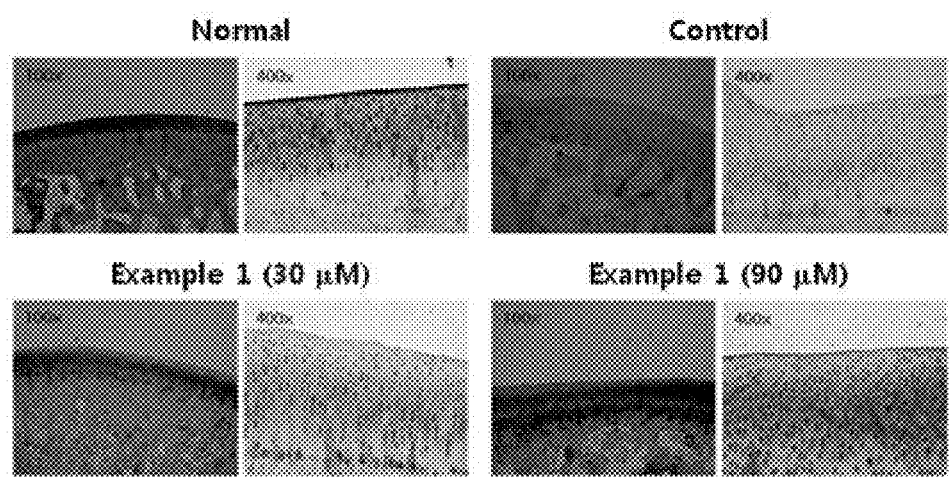
FIG. 10 illustrates the results of cartilage regeneration effects confirmed with Safranin O staining in a degenerative arthritis model, in accordance with an embodiment of the present invention.

The results of staining (Safranin O) of proteoglycan in the cartilage matrix are shown in FIG. 10. As shown in FIG. 10, the control group (lactose-administered group) exhibited remarkably decreased synthesis of proteoglycan in the middle layer and the deep layer, as compared to the normal group. On the other hand, the experimental group (group to which the peptide of Example 1 was administered) exhibited increased synthesis of proteoglycan in a dose-dependent manner. Therefore, it was demonstrated that, with regard to the experimental group, the peptide of Example 1 increases the synthesis of proteoglycan, a major matrix component of articular cartilage tissue, thereby promoting regeneration of damaged cartilage tissue.

Figure 11:
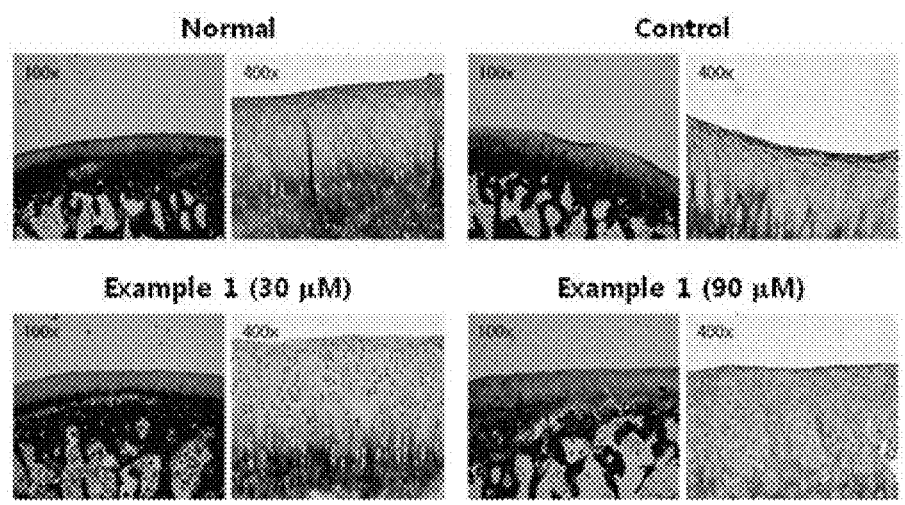
FIG. 11 illustrates the results of cartilage regeneration effects confirmed with Masson's Trichrome staining in a degenerative arthritis model, in accordance with an embodiment of the present invention.

The results of collagen staining (Masson's Trichrome) are shown in FIG. 11. As shown in FIG. 11, the normal group and the experimental group (group to which the peptide of Example 1 was administered) exhibited similar staining patterns, whereas the damaged region of the control group (lactose-administered group) exhibited intense staining which reflects increased synthesis of fibrocollagen in the damaged region. Accordingly, it was demonstrated that the peptide of Example 1 promotes the regeneration of cartilage tissue having a normal surface (hyaline cartilage, mainly collagen type II), whereas the control group (lactose-administered group) exhibited increased synthesis of fibrocartilage (mainly collagen type I) which is susceptible to damage due to weakening of physical properties as a result of the adaptive process to degenerative changes.

Increased synthesis of fibrocollagen observed from the collagen staining results of the control group (lactose-administered group) corresponds to the results of an increase in fibrochondrocytes on the superficial layer, which was observed in the damaged region of the control group upon carrying out H&E staining, thus demonstrating that normal tissue regeneration is not induced in the adaptive process to degenerative changes, but the peptide of Example 1 induces regeneration of normal tissue in the experimental group.

As a result, it was demonstrated that the peptide of Example 1 promotes the activation of chondrocytes and the synthesis of cartilage matrix components (proteoglycan, collagen type II) in experiments using a degenerative osteoarthritis model and therefore has excellent effects of regenerating damaged cartilage tissue similar to normal tissue.

[Industrial Applicability]

The present invention provides a peptide or a pharmaceutically acceptable salt thereof, a composition containing the same peptide or a pharmaceutically acceptable salt thereof as an active ingredient, and a composition containing the same peptide or a pharmaceutically acceptable salt thereof and TGFβ1, for the treatment and/or prevention of at least one selected from cartilage damage and arthritis. The above-mentioned peptide or a pharmaceutically acceptable salt thereof is effective for the treatment and/or prevention of cartilage damage and/or arthritis and is capable of exhibiting effects on the regeneration of cartilage tissue, the inhibition of the expression of cartilage tissue matrix degrading enzyme and/or the inhibition of cartilage tissue ossification, and are therefore industrially applicable.

The invention claimed is:

1. An isolated peptide consisting of the amino acid sequence of formula (I)

$$X1\text{-}Leu\text{-}X2\text{-}Leu\text{-}X3 \qquad (I)$$

or pharmaceutically acceptable salt thereof,
  wherein X1 is Glu or Asp; X2 is His, Lys or Arg; X3 is Asp or Glu, and Glu, Asp, Leu, His, Lys, and Arg are glutamic acid, aspartic acid, leucine, histidine, lysine, and arginine, respectively.

2. An isolated peptide consisting of the amino acid sequence of SEQ ID NO: 1 (Glu-Leu-His-Leu-Asp) or pharmaceutically acceptable salt thereof,
  wherein and Glu, Asp, Leu, His, Lys, and Arg are glutamic acid, aspartic acid, leucine, histidine, lysine, and arginine, respectively.

3. A composition comprising the peptide of claim 1 or a pharmaceutically acceptable salt thereof as an active ingredient.

4. The composition according to claim 3, wherein the composition is a pharmaceutical composition.

5. A composition comprising the peptide of claim 1 or a pharmaceutically acceptable salt thereof and transforming growth factor beta 1 (TGFβ1).

6. A composition comprising the peptide of claim 2 or a pharmaceutically acceptable salt thereof as an active ingredient.

7. A composition comprising the peptide of claim 2 or a pharmaceutically acceptable salt thereof and transforming growth factor beta 1 (TGFβ1).

8. The composition of claim 3, wherein administering the composition promotes the production of type II collagen.

\* \* \* \* \*